(12) United States Patent
Jones et al.

(10) Patent No.: US 7,114,009 B2
(45) Date of Patent: Sep. 26, 2006

(54) ENCAPSULATING FIBRE CHANNEL SIGNALS FOR TRANSMISSION OVER NON-FIBRE CHANNEL NETWORKS

(75) Inventors: Loren M. Jones, San Jose, CA (US); Stanford L. Helton, San Jose, CA (US); Allison Parson, Los Gatos, CA (US); Rendell K. Fong, San Jose, CA (US); Edward G. Carmona, Pleasanton, CA (US); Emmanuel W. Jee, San Jose, CA (US)

(73) Assignee: San Valley Systems, San Jose, CA (US)

( * ) Notice: Subject to any disclaimer, the term of this patent is extended or adjusted under 35 U.S.C. 154(b) by 884 days.

(21) Appl. No.: 09/811,155

(22) Filed: Mar. 16, 2001

(65) Prior Publication Data

US 2002/0133629 A1  Sep. 19, 2002

(51) Int. Cl.
*G06F 15/16* (2006.01)

(52) U.S. Cl. .............. 709/250; 709/230; 709/231; 709/232; 709/236; 709/238; 709/246; 709/249; 370/466

(58) Field of Classification Search .............. 709/231, 709/232, 246, 249, 230, 236, 238, 250; 370/466
See application file for complete search history.

(56) References Cited

U.S. PATENT DOCUMENTS

| | | | | |
|---|---|---|---|---|
| 5,809,341 A * | 9/1998 | Nimishakvi et al. | ........... | 710/60 |
| 6,014,370 A * | 1/2000 | Komatsu et al. | ............ | 370/248 |
| 6,098,125 A * | 8/2000 | Fiacco et al. | ................ | 710/52 |
| 6,188,668 B1 * | 2/2001 | Brewer et al. | .............. | 370/222 |
| 6,272,551 B1 * | 8/2001 | Martin et al. | ............... | 709/250 |
| 6,400,730 B1 * | 6/2002 | Latif et al. | ................... | 370/466 |
| 6,738,821 B1 * | 5/2004 | von Stamwitz et al. | .... | 709/230 |
| 6,765,871 B1 * | 7/2004 | Knobel et al. | ............. | 370/231 |
| 2001/0002901 A1 * | 6/2001 | Henson | ....................... | 370/242 |
| 2001/0009547 A1 * | 7/2001 | Jinzaki et al. | ............. | 370/390 |
| 2002/0061018 A1 * | 5/2002 | Chien | ......................... | 370/389 |
| 2002/0176526 A1 * | 11/2002 | Mejia | ......................... | 375/372 |

FOREIGN PATENT DOCUMENTS

WO    WO 01/44891    6/2001

* cited by examiner

*Primary Examiner*—Nabil El-Hady
(74) *Attorney, Agent, or Firm*—Pillsbury Winthrop Shaw Pittman LLP (57) ABSTRACT

A method for communicating between a first Fibre Channel (FC) enabled device and a second FC enabled device, where the communication occurs across a fabric that operates in accordance with a first protocol different from a FC protocol of the first and second FC enabled devices. The method includes receiving, from the first FC enabled device, at a first gateway receiver a sequence of bytes including at least one control character in accordance with the FC protocol. The method then includes replacing the at least one control character with at least one data character. The method also includes generating an encapsulation header and an encapsulation footer for encapsulating the sequence of bytes in which at least one control character was replaced with at least one data character. The method then includes setting a control character indicator in the encapsulation header if a first byte in the sequence of bytes received at the gateway receiver is a control character. The method includes setting an end of frame indicator in the encapsulation footer if a last byte in the sequence of bytes received at the first gateway receiver is an end of frame control character.

27 Claims, 9 Drawing Sheets

ENCAPSULATING FIBRE CHANNEL SIGNALS FOR TRANSMISSION OVER NON-FIBRE CHANNEL NETWORKS

FIELD

The present invention pertains to the field of storage area networks. More particularly, the present invention relates methods and systems for communicating with and between storage area networks.

BACKGROUND

Fibre Channel is a computer communications protocol designed to meet the many requirements related to the ever increasing demand for high performance information transfer. The Fibre Channel protocol is sometimes referred to in the literature as Fiber Channel; the variation is due to differences in spelling between American English and British English. Fibre Channel combines the benefits of both channel and network technology and also provides for flexible topologies, connectivity over several kilometers (not to exceed generally 10 kilometers (km)), and support for multiple relatively high data rates, media types, and connectors. Fibre Channel has become relatively popular for connecting multiple storage devices together in a storage area network (SAN). The popularity is partly due to the fact that once a channel between two devices is set up very little decision making is needed, allowing for a high speed, hardware intensive environment.

Unfortunately, communication between and with storage area networks cannot be met with existing Fibre Channel networks. Increasingly storage area networks are becoming geographically dispersed. This dispersion is due to many factors: mergers and acquisitions of companies located nationally and internationally; desire to provide off-site storage; and storage replication, among other factors. Due to the upper limit on the distance of about 10 km between two devices on a Fibre Channel network, it is unpracticable to interconnect two storage area networks that are separated by a distance greater than 10 km using Fibre Channel.

Several solutions have been proposed for interconnecting geographically dispersed SANs. However, the proposed solutions are unsatisfactory for a variety of shortcomings. For example, the proposed solutions often involve the establishment of a non-Fibre Channel network (or point-to-point interconnect) with a proprietary protocol and hardware for transporting Fibre Channel frames over large distances (greater than 10 km). Furthermore, the solutions often involve the establishment of a network (or point-to-point interconnect) that is parallel to wide area networks (WANs) and metropolitan area networks (MANs) that communicate over large distances via standard non-proprietary protocols. Many national and international carriers operate MANs and WANs in accordance with Asynchronous Transfer Mode (ATM), Transfer Control Protocol/Internet Protocol (TCP/IP), and Synchronous Optical Network (SONET), among other protocols. These networks leverage the economy scale afforded by a large number of independent users to provide a relatively economical service. In contrast to these networks which provide a cost-effective solution for communication over large distances, the parallel network may be relatively costly, inefficient and needlessly redundant. For example, the parallel network requires separate management and maintenance effort and does not benefit from the economy of scale due to many users using the same network.

As described above, existing solutions are not capable of providing efficient, non-proprietary, and relatively economical communication between geographically dispersed SANs. Consequently, it is desirable to interconnect geographically dispersed Fibre Channel enabled SANs using the standard protocols of non-Fibre Channel networks that can provide a relatively economical and efficient solution.

SUMMARY

According to an embodiment of the invention, a method for communicating between a first Fibre Channel (FC) enabled device and a second FC enabled device, where the communication occurs across a fabric that operates in accordance with a first protocol different from a FC protocol of the first and second FC enabled devices is described. The method includes receiving, from the first FC enabled device, at a first gateway receiver a sequence of bytes including at least one control character in accordance with the FC protocol. The method then includes replacing the at least one control character with at least one data character. The method also includes generating an encapsulation header and an encapsulation footer for encapsulating the sequence of bytes in which at least one control character was replaced with at least one data character. The method then includes setting a control character indicator in the encapsulation header if a first byte in the sequence of bytes received at the gateway receiver is a control character. The method includes setting an end of frame indicator in the encapsulation footer if a last byte in the sequence of bytes received at the first gateway receiver is an end of frame control character.

BRIEF DESCRIPTION OF THE DRAWINGS

The present invention is illustrated by way of example, and not limitation, in the figures of the accompanying drawings in which like references denote similar elements, and in which:

FIG. 5b illustrates four ethernet packets corresponding to an FC frame;

DETAILED DESCRIPTION

A method and apparatus for communicating between two Fibre Channel enabled devices is described, where the communication occurs across a fabric that operates in accordance with a protocol different from the protocol of the two Fibre Channel enabled devices. In the following description, for purposes of explanation, numerous specific details are set forth in order to provide a thorough understanding of the present invention. It will be evident, however, to one skilled in the art that the present invention may be practiced in a variety of communication systems, especially Fibre Channel to Gigabit Ethernet systems, without these specific details. In other instances, well known operations, steps, functions and devices are not shown in order to avoid obscuring the invention.

Parts of the description will be presented using terminology commonly employed by those skilled in the art to convey the substance of their work to others skilled in the art, such as routers, protocols, gateways, fabric, networks, storage area networks, and so forth. Also parts of the description will also be presented in terms of operations performed through the execution of programming instructions or initiating the functionality of some electrical component(s) or circuitry, using terms such as, performing, sending, processing, packaging, scheduling, transmitting, configuring, and so on. As well understood by those skilled in the art, these operations take the form of electrical or magnetic or optical signals capable of being stored, transferred, combined, and otherwise manipulated through electrical or electromechanical components.

Various operations will be described as multiple discrete steps performed in turn in a manner that is most helpful in understanding the present invention. However, the order of description should not be construed as to imply that these operations are necessarily performed in the order that they are presented, or even order dependent. Lastly, repeated usage of the phrases "in one embodiment," "an alternative embodiment," or an "alternate embodiment" does not necessarily refer to the same embodiment, although it may.

Figure 1:
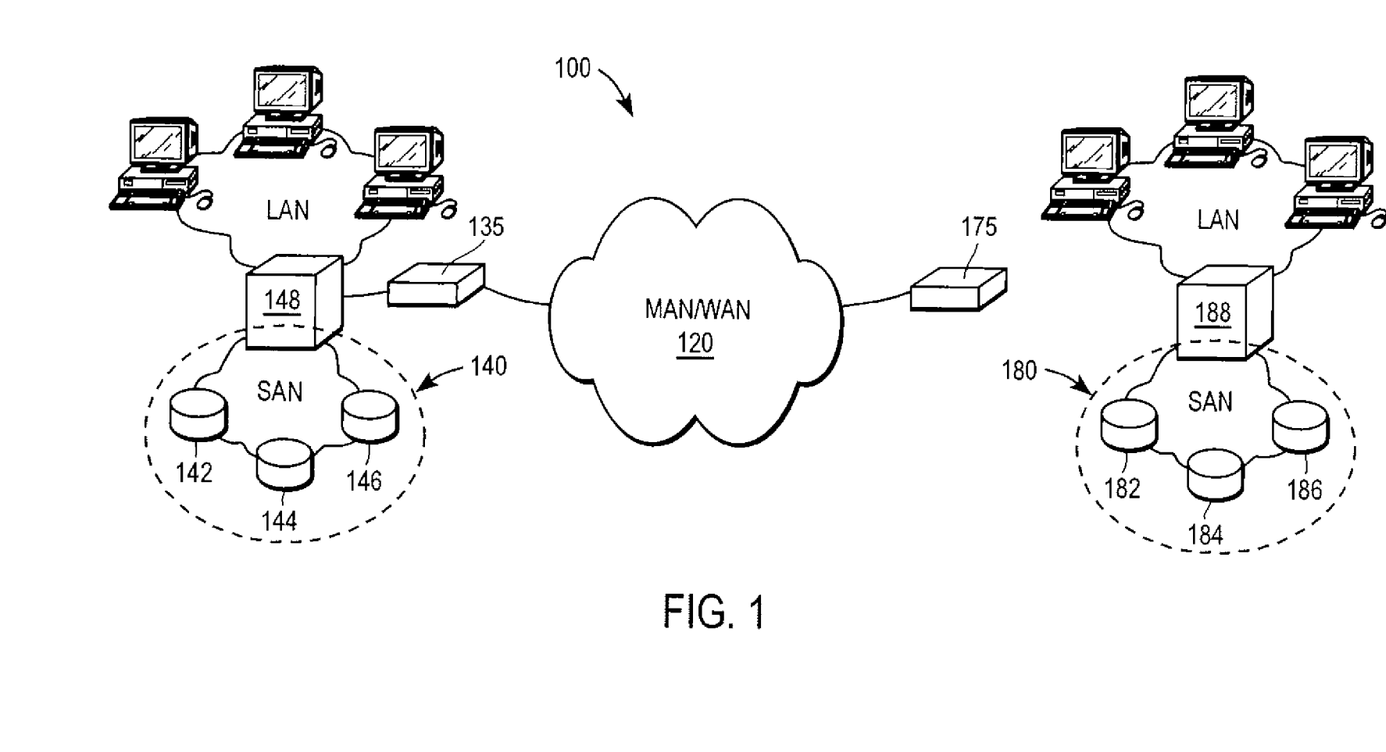
FIG. 1 illustrates a block diagram of an inter-network including fabric, gateways, and storage area networks (SANs)

FIG. 1 illustrates a block diagram of an inter-network 100 including fabric 120, gateways 135 and 175, and storage area networks (SANs) 140 and 180. In one embodiment in accordance with the present invention, storage area network 140 and 180 operate in accordance with the Fibre Channel (FC) computer communications protocol (FC protocol) as described in American National Standards Institute (ANSI) X3.-240-1994, Fibre Channel Physical and Signaling Interface specification (FC-PH). Each of the networks 140 and 180 can be a combination of storage devices, such as disk drives 142, 144, 146, 182, 184, 186, and servers 148 and 188. Fabric 120 comprises a network operating in accordance with the Gigabit Ethernet protocol as described in any of the following standards: IEEE Standard 802.3ad-2000 for Information Technology—Local and Metropolitan Area Networks—Part 3: Carrier Sense Multiple Access with Collision Detection (CSMA/CD) Access Method and Physical Layer Specifications-Aggregation of Multiple Link Segments; IEEE Standard 802.3ab-1999 for Information Technology—Telecommunications and information exchange between systems—Local and Metropolitan Area Networks—Part 3: Carrier Sense Multiple Access with Collision Detection (CSMA/CD) Access Method and Physical Layer Specifications—Physical Layer Parameters and Specifications for 1000 Mb/s Operation over 4 pair of Category 5 Balanced Copper Cabling, Type 1000BASE-T; Computer/Local & Metropolitan Area Networks; IEEE Standard 802.3ac-1998 for Information technology—Telecommunications and information exchange between systems—Local and metropolitan area networks—Specific requirements Part 3: Carrier sense multiple access with collision detection (CSMA/CD) frame extensions for Virtual Bridged Local Area Networks (VLAN) tagging on 802.3 networks. Fabric 120 may include multiple local networks, bridges, and routers in a wide area network (WAN) or a metropolitan area network (MAN). The manner of operation of fabric 120 is not described here because it understood well by those of ordinary skill in the art.

In one embodiment, SANs 140 and 180 operate at a rate of 1.0625 gigabits/sec and fabric 120 operates at a rate of 1.25 gigabits/sec. In alternative embodiments, SANs 140 and 180, and fabric 120 may operate at other rates.

Even though SANs 140 and 180, on the one hand, and fabric 120, on the other hand, use different protocols, devices in SANs 140 and 180 can communicate with or transfer data between each other because they are coupled to fabric 120 by gateways 135 and 175, respectively. As will be described below, gateways 135 and 175 take FC frames or signals (primitives or primitive sequences) received from networks 140 and 180, respectively, and process them to generate ethernet packets suitable for transmission on fabric 120. Additionally, gateways 135 and 175 take ethernet packets received from fabric 120 and intended for either of SANs 140 and 180, respectively, and process them to generate FC frames or signals suitable for transmission over SANs 140 and 180, respectively. As will be described in the following paragraphs, gateways 135 and 175 allow network 140 and 180, respectively, to seem to be coupled by a FC fabric instead of an ethernet fabric. Accordingly, a device on network 140 is able to communicate with a device on network 180, and vice versa, through the gateways and fabric, using FC signals.

Before describing the establishment of a communications link and data transfer between a device on network 140 and network 180, some useful background information on the nature of FC frames and signals, and ethernet packets is provided. Additionally, a novel solution to a problem that may be encountered in the transmission of FC frames or signals over a non-FC network is described.

All information in Fibre Channel is transmitted as groups of four transmission characters, each of which is one byte in length, called transmission words. Some transmission words have a K28.5 character as the first transmission character. Groups of four transmission characters which have a K28.5 character as the first transmission character are called ordered sets. Some ordered sets mark the beginning and end of frames (frame delimiters). Others convey information in between frames in the form of primitive indications (a single ordered set) and primitive sequences (a stream of the same ordered set). Examples of ordered sets are: start of frame (SOF), end of frame (EOF), idle, receiver_ready (R_RDY), and several others. Examples of a stream of the same ordered set are: link reset (LR), link reset response (LRR), not operational (NOS), offline (OLS), and others. Some of the primitive sequences are used to set up the communication channel that is needed before data transfer can occur between two Fibre Channel enabled devices.

Ethernet also uses K28.5 characters in its packets to setup a circuit between two devices and to determine where different segments of a sequence of characters begin and end. Since both FC and ethernet use K28.5 characters, placing FC primitives, primitive sequences, and frames on the ethernet enabled fabric 120 would cause routers and other devices in fabric 120 to be confused, resulting in improper operation. The present invention recognizes the cause of the improper operation and provides a method and system for modifying FC primitives, primitive sequences, and data frames and adding additional information to prevent this improper operation.

Figure 2A:
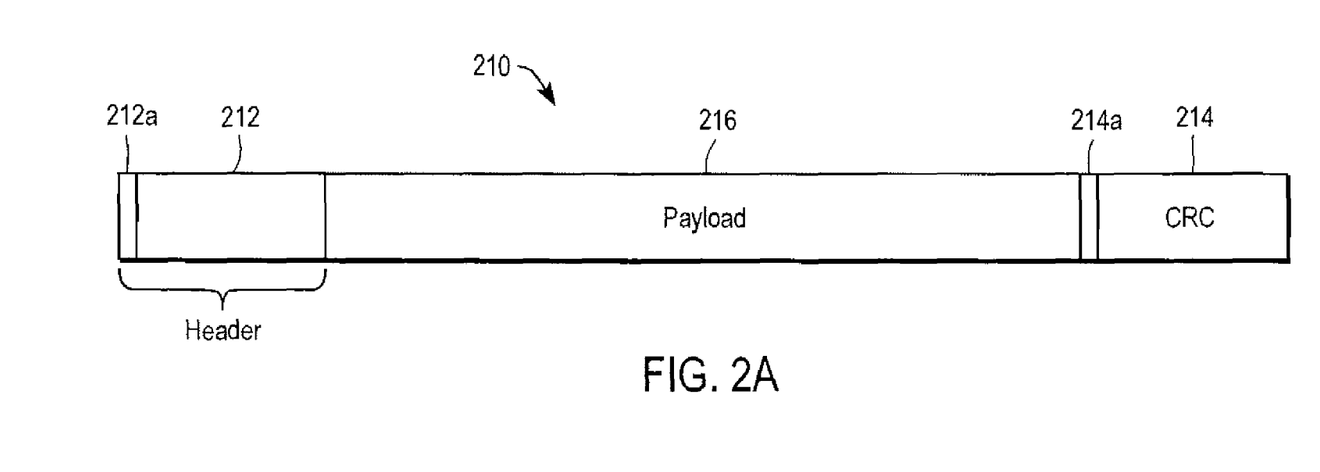
FIG. 2a illustrates an ethernet packet having an ethernet header, and payload area.
Figure 2B:
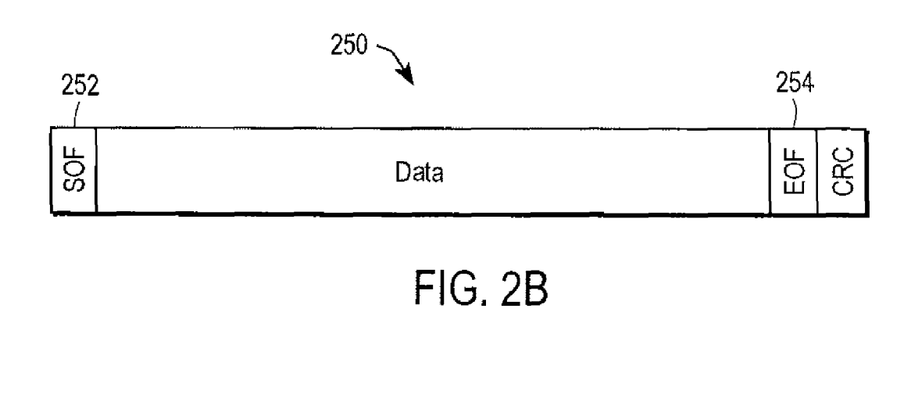
FIG. 2b illustrates a FC frame with K28.5 characters.

FIG. 2a illustrates an ethernet packet having an ethernet header, payload area, and cyclic redundancy check (CRC) bits. Preamble 212 of ethernet packet 210 has at least one K28.5 characters 212a. Packet 210 is representative of packets that are generated at gateway 140 and travel to gateway 180 via fabric 120. FIG. 2b illustrates a FC frame with K28.5 characters. Frame 250 is representative of frames generated by a device in SAN 140 for transmission to a device in SAN 180 or other devices in SAN 140. For example, device 142 generates frame 250 for transmission to device 182. Gateway 135 receives frame 250. If gateway 135 were to place a FC frame, such as frame 250, that has K28.5 characters 252, 254 in payload area 216 of packet 210, it would cause improper processing of packet 210 as it traveled on fabric 120. Routers (not shown) in fabric 120 would improperly process packet 120 because K28.5 characters of frame 250 would be confused with the K28.5 characters of the ethernet packet 210. The present invention provides a novel solution for this problem by replacing the K28.5 characters in frame 250 with D28.5 characters before placing frame 250 in payload 216 of packet 210. The invention also includes adding a header and footer to frame 250. The header and frame allow the reconstruction of frame 250 at gateway 175 such that after reconstruction gateway 175 has a duplicate of the frame that was sent by device 142. Since the frame that was sent by device 142 had K28.5 characters, after reconstruction, frame 250 will have K28.5 characters in the place of D28.5 characters. With its K28.5 characters back, frame 250 can travel from Gateway 175 to device 182 over the FC enabled network 180.

The above process of replacing the K28.5 characters with D28.5 characters and adding an encapsulation header and encapsulation footer to a FC frame is referred to herein as encapsulation. The process of reconstructing the FC frame so as to return the K28.5 characters which were replaced by D28.5 characters is referred to herein as decapsulation.

Figure 3:
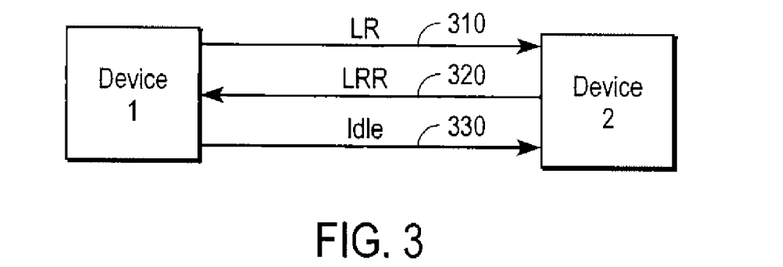
FIG. 3 illustrates the sequence of transmissions that are sent to set up a communications link and transfer data between two FC enabled devices.

Having generally described the process of modifying an FC frame to permit transmission from a device in SAN 140 to a device in SAN 180, the process of encapsulation and decapsulation will be described in greater detail in the contexts of setting up a communications link and data transfer between two FC devices in SANs 140 and 180. Before data can be transmitted between two FC enabled devices, a communications link (or channel) needs to be set up. A communications link is set up by transmitting primitive sequences from one device to another. Examples of primitive sequences include link reset (LR), link reset response (LRR), not operational (NOS), current and offline (OLS). FIG. 3 illustrates the sequence of transmissions that are sent to set up a communications link and transfer data between two FC enabled devices. To set up a communications link a first device transmits an LR signal 310 to second device. The second device responds with LRR signal 320. The first device then sends an idle signal 330, indicating it is ready to attempt FC loop initialization. The first device then sends data to the second device. Alternatively, there could be a "full handshake" between the devices. In a full handshake, the first device sends an LR signal to the second device which then responds with an LR signal to the first device. The first device then sends an LRR signal to the second device which then responds with an LRR signal to the first device. The first device then sends an idle signal to the second device and the second device responds with an idle signal.

For purposes of illustration, the set up of a communications link and data transfer between device 142 and device 182 is described below in greater detail. It should be appreciated that communications links and data transfers between other devices in networks 140 and 180 can be made in a similar manner and need not be described here. For two FC devices to set up a communications link, one device has to first "find" the other device. Device 142 queries the name server (not shown) on server 148 to check about device 182. Server 148 in turn queries server 188 to check if device 182 is registered. Server 188 responds to server 148 that device 182 is registered. In turn server 148, responds to device 142 that device 182 is registered.

Figure 4A:
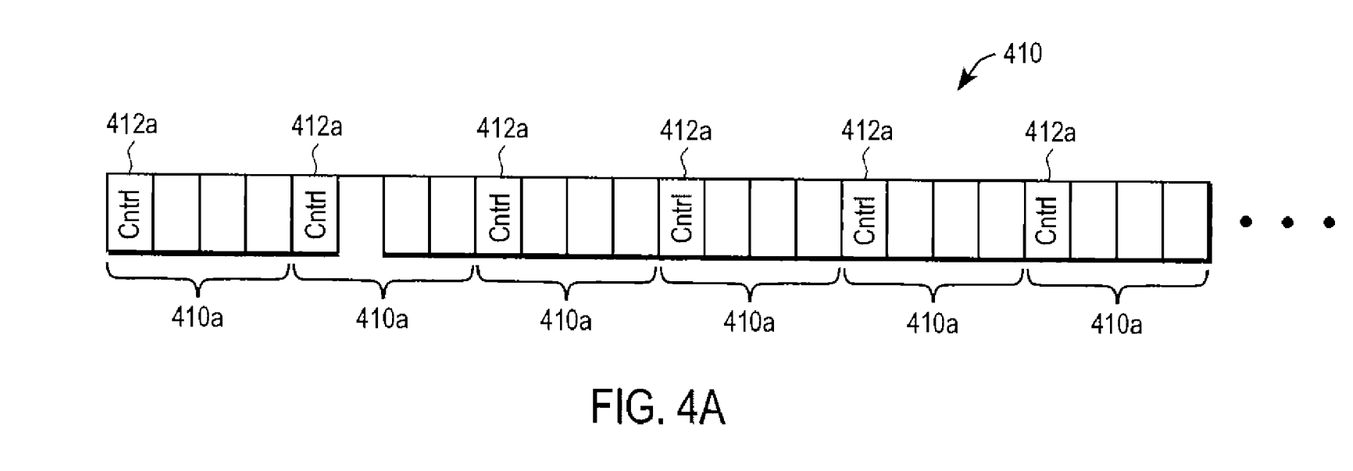
FIG. 4a illustrates an LR sequence with multiple K28.5 characters.

Having established the availability of device 182 on the network, device 142 proceeds to initialize the communications link between the devices. To initialize the link, device 142 sends a LR sequence to server 148. FIG. 4a illustrates an LR sequence. LR sequence 410 has many LR words 410a each of which has a K28.5 character 412a. An LR sequence may be made of many LR words 410a, in some embodiments a 100 or more LR words. As server 148 receives each word of sequence 410, it forwards the word to gateway 135.

Figure 4B:
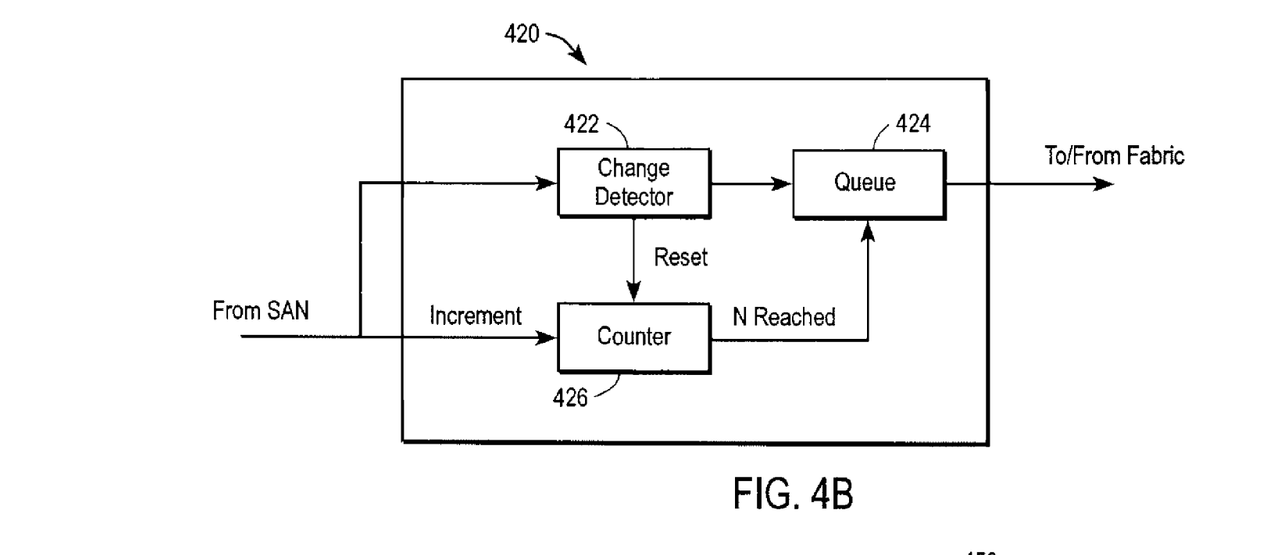
FIG. 4b illustrates an encapsulated LR sequence.

According to one embodiment, gateway 135 forwards only some of the LR words (an abridged primitive sequence) in sequence 410 to gateway 175. FIG. 4b illustrates a bandwidth conservation circuitry. Gateways 135 & 175 each has bandwidth conservation circuitry 420. Circuitry 410 prevents gateway 135 from needlessly felling the gateway 135-gateway 175 link with repetitive information. Circuitry 420 extracts N LR words from sequence 410 and forwards the abridged primitive sequence to gateway 175.

Referring to FIG. 4b, link change detector 422 receives words sent by device142. If detector 422 detects a change in the words (e.g., change from RRDY to Idle, or LR to LRR), a reset signal to set counter 426 to zero is applied to counter 426. The words received from device 142 are stored in queue 424 which implements a first-in-first-out scheme. Also, as each word is received, counter 426 is incremented. When counter 426 reaches the threshold N, the words that are in queue 424 are extracted and sent out to gateway 175. Subsequent words that arrive after the threshold is reached and that are the same type as the N words are not transmitted to gateway 175. When a word arrives that is of a different type than the N words, detector 422 resets counter 426 and the process described above is repeated. While queue 424 is emptied when counter 426 reaches N, it should be appreciated that queue 424 may have more than N words when it is emptied and its words are transmitted to gateway 175.

Gateway 134 has an inactivity counter (not shown) which has a value N. Gateway 134 extracts N of the LR words in the LR sequence and transmits them to gateway 175. The inactivity counter prevents gateway 135 from clogging the gateway 135-gateway 175 link with repetitive information. If N identical words, in a sequence of words, arrive at gateway 135, gateway 135 relays the N words and any preceding words, which do not have a sequence of N identical words in them, to gateway 175.

Any words which come after the N words and are of the same type as the N words are ignored. So for example, if a sequence of 100 LR words is sent to gateway 175 from device 142, only N LR words will be forwarded to gateway 175. According to one embodiment, the selection of the value N is a function of the transmission rate between device 142 and server 148, the transmission rate between gateway 135 and gateway 175, and the overhead required by other layers of the protocol to transmit the N words. N is chosen such that if two groups of N are to be sent immediately one after the other, the amount of time the two groups of N take to be transmitted on the device 142-gateway 135 link is equivalent to the amount of time the two groups of N plus the overhead take to be transmitted on the gateway 135-gateway 175 link. The equation below shows the relationship among N, the speed on the device 142-gateway 135 link ($R_1$), the speed on the gateway 135-gateway 175 link ($R_h$), and the overhead words:

$$(N+N)/R_1 = (N+N+\text{overhead words})/R_h$$

Figure 4C:
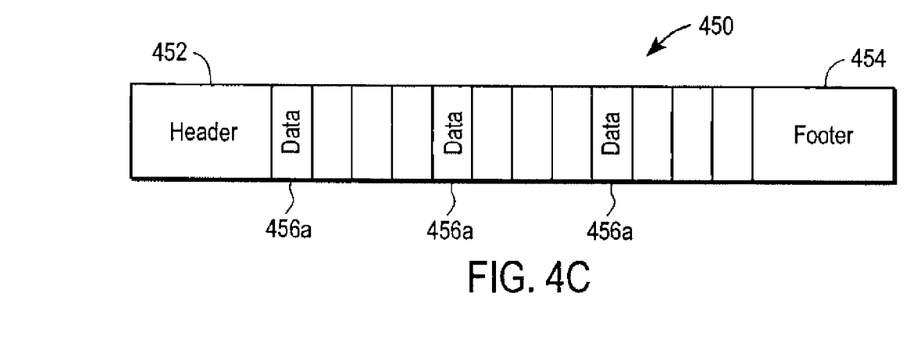
FIG. 4c illustrates bandwidth conservation circuitry.

Since ethernet and Fibre Channel are different and incompatible protocols, gateway 135 does not immediately forward the N LR words. Rather, gateway 135 first replaces K28.5 characters 412a with D28.5 characters and encapsulates the N LR words by placing a header and footer around the N LR words. The header and footer are needed by gateway 175 to replace K28.5 characters in an encapsulated LR sequence that arrives at gateway 175 with D28.5 characters. FIG. 4c illustrates an encapsulated abridged LR sequence. Abridged LR sequence 450 represents LR sequence 410 after gateway 135 extracts 3 LR words, encapsulates them with header 452 and footer 454 and replaces the K28.5 characters with D28.5 characters 456a. After encapsulation, primitive sequence 450 is then made the payload of an ethernet packet (not shown).

Figure 4D:
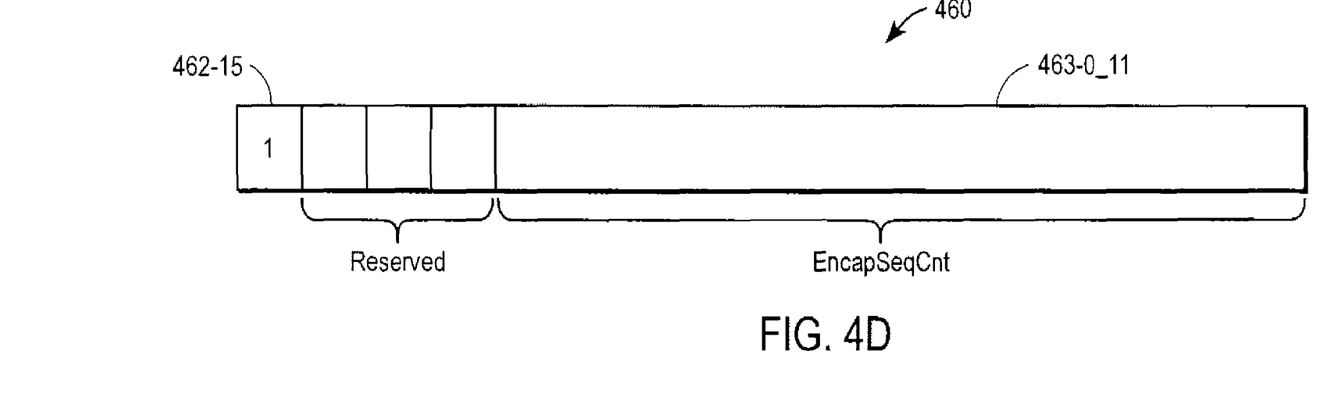
FIG. 4d illustrates an encapsulation header in greater detail.

FIG. 4d illustrates an encapsulation header in greater detail. The header has 16 bits. In one embodiment, header 460 contains a control bit and a 12 bit encapsulation sequence count (EncapSeqCnt). Bit 462-15 (DorK bit) identifies whether the first word of the FC signal that is placed in the ethernet payload is a data word or a K28.5 word. As stated above, K28.5 characters are not allowed in the ethernet payload. Consequently, for proper decapsulation an indicator is needed in the header to indicate that the first word of the FC signal is really a K28.5 character rather than a data character. Since the first character of the LR sequence is a K28.5 character, bit 462-15 is set to 1 as shown in FIG. 4c.

Bits 462-0_11 (or EncapSeqCnt) are used to uniquely identify an FC frame among other transmitted/received frames and aids in the detection of lost frames across the ethernet network. If a frame is received with an out of sequence EncapSeqCnt, the gateway recognizes this as an indication that a frame has been lost. The frame just received and subsequent frames received are thrown away until a frame with a set DorK bit is received. This frame indicates the beginning of a new FC frame sequence and informs the bridge to resume normal frame reception.

Figure 4E:
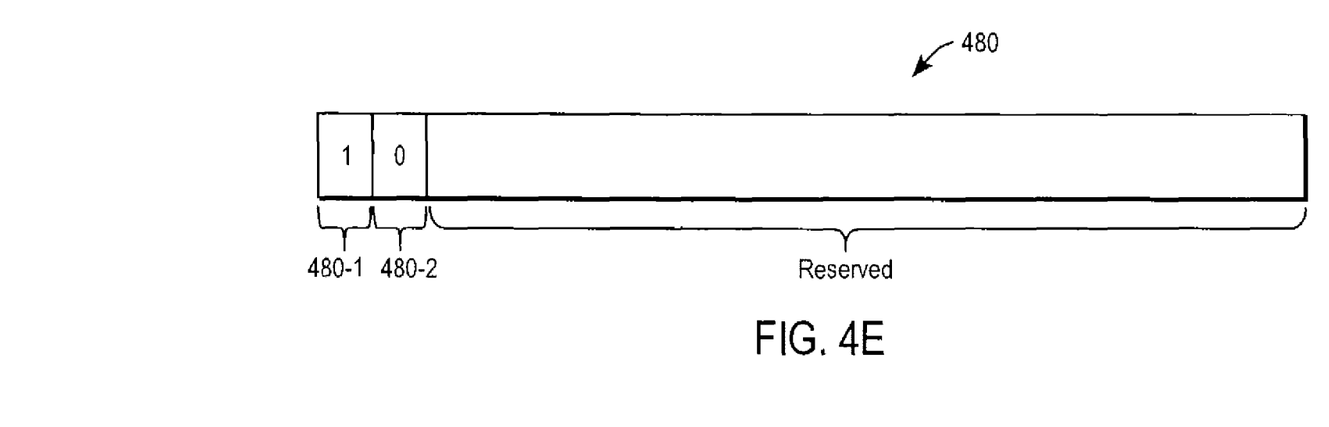
FIG. 4e illustrates an encapsulation footer in greater detail.

FIG. 4e illustrates an encapsulation footer in greater detail. The footer has 32 bits. In one embodiment, footer 480 contains a DorK bit 480-1, a control bit 480-2 (EncapEOF) and a 30 reserved bit field. DorK bit 480-1 indicates whether the preceding word contains a data character that is to be changed to a control character. EncapEOF indicates whether the current ethernet payload is the end of a FC data frame and should, therefore, contain a FC EOF. As indicated above, EOF and other K28.5 characters are not allowed in the ethernet packet payload. Consequently, a footer must be appended to an FC frame segment that contained an EOF that was replaced with a D28.5 character. The footer indicates that the current ethernet payload is the last segment of an FC frame. Since the payload of the ethernet packet is an LRR sequence rather than an FC data frame with a D28.5 character which was substituted for a K28.5 EOF character, EncapEof is not set as shown in FIG. 4e.

After encapsulation and placement of a modified FC frame into the payload of an ethernet packet, the ethernet packet is transmitted from gateway 135 through fabric 120 to gateway 175. The manner by which an ethernet packet arrives at gateway 175 by way of fabric 120 need not be described here because it is well known in the art.

Gateway 175 receives the ethernet packet and determines whether the payload is an FC signal intended for device 182. If the payload is an FC signal intended for device 182, gateway 175 decapsulates the FC signal. To decapsulate the FC signal and reconstruct the FC signal received at gateway 135 from server 148, gateway 175 examines the header and footer. If the header's DorK bit is set, the data characters in the FC signal are changed to control characters. If the EncapEOF of the footer is set, the last word is changed to an EOF character. According to one embodiment, the header and footer are removed after replacement of the data characters is made. In an alternative embodiment, the header and footer are removed before the replacement is made. Gateway 175 examines the reconstructed FC signal to determine whether a primitive sequence has been received. If a primitive sequence has been received, gateway 175 continuously transmits the words of the primitive sequence to device 182.

It should be appreciated that an LRR sequence which is transmitted from device 182 to device 142 is processed by gateway 175 in a manner similar to the manner in which the LR sequence was processed by gateway 135. Consequently, the processing of the LRR sequence by gateway 175 need not be described here.

After an LR sequence is sent from device 142 to 182 and an LRR sequence is received by device 142 from device 182, a channel is set up between devices 142 and 182. Having set up a channel or communications link, data transfer can now occur between devices 142 and 182.

Figure 5A:
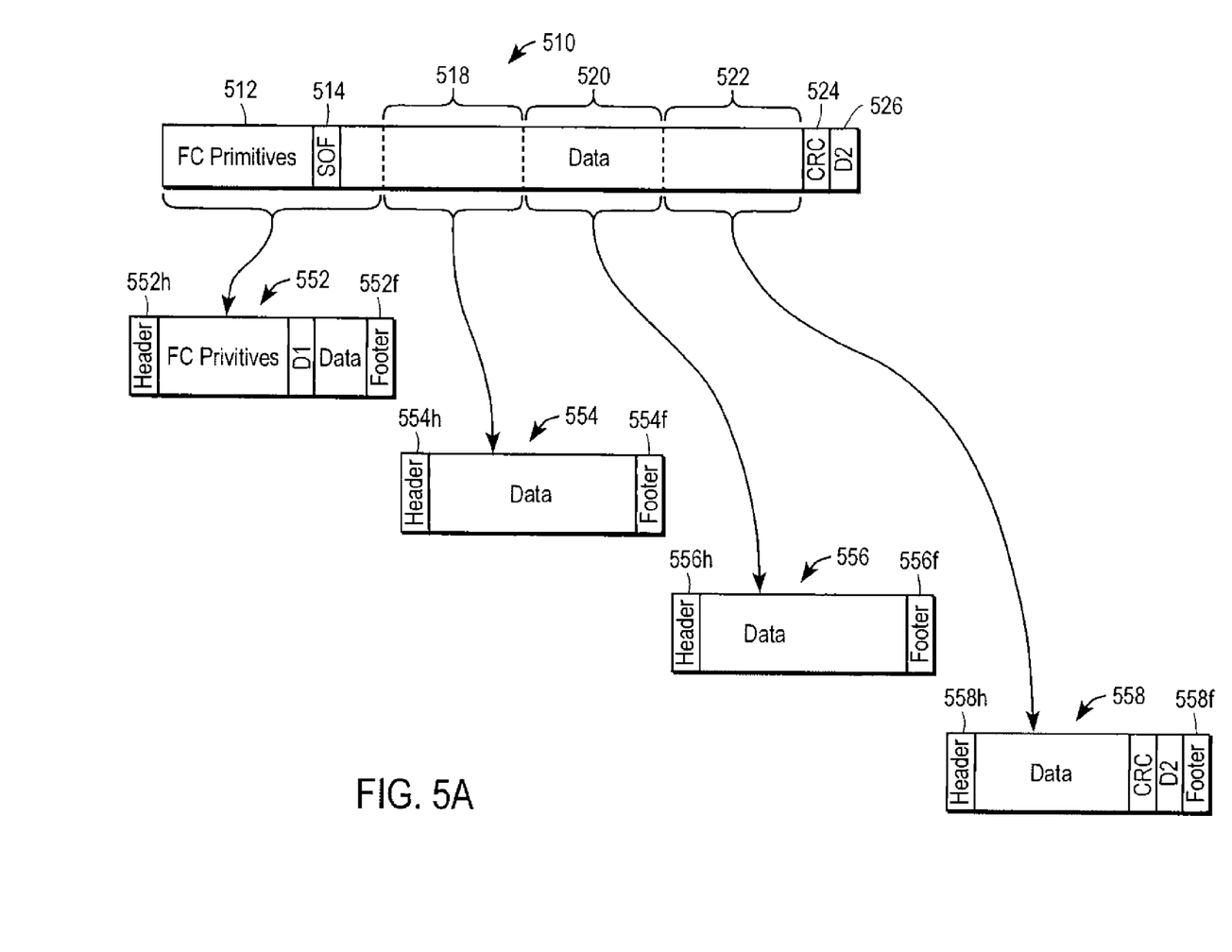
FIG. 5a illustrates an FC frame having a length that exceeds an ethernet maximum transfer unit (MTU) length.

FIG. 5a illustrates an FC frame having a length that exceeds an ethernet maximum transfer unit (MTU) length. In one embodiment, the ethernet maximum transfer unit (MTU) is 512 bytes. With respect to the transmission of data, Fibre Channel defines a variable length frame consisting of 36 bytes of overhead and up to 2112 bytes of payload for a total maximum size of 2156 bytes. The total size of the frame must be an even multiple of four bytes so that partial transmission words are not sent. Between 0 and 3 pad bytes are appended to the end of the payload to satisfy this rule. A Start of Frame (SOF) delimiter and End of Frame (EOF) delimiter mark the beginning and end of each Fibre Channel frame. A 32-bit CRC is added after an EOF. Frame 510 includes FC primitives 512, SOF 514, data 516, data 518, data 520, data 522, CRC 524, and EOF 526. Device 142 generates frame 510 for transmission to gateway 135. Since frame 510 is about four times as long as the MTU, gateway 135 divides frame 510 across four consecutive ethernet packets. FIG. 5b illustrates four encapsulated packets corresponding to an FC frame. Packet 552 has a corresponding header 552h. The first bit of header 552h is set indicating that the first word following the header was a control word (FC primitive) in the section of the FC frame that was encapsulated. Since the remaining packets 554, 556, 558 are encapsulations of only FC data, the first bit of headers 554h, 556h, 558h are not set. The EncapSeqCnt field of headers 552h, 554h, 556h, 558h increase in increments of 1 starting with N. The EncapSeqCnt field is used to reconstruct, in the right order, the FC frame from the data segments that were placed in the four ethernet packets.

Packets 552, 554, 556 each have a corresponding footer 552f, 554f, 556f, respectively. The most significant bit of each of footers 552f, 554f, 556f is 0 indicating that an EOF was not in the section of the FC frame that was encapsulated. On the other hand, the second bit of footer 558f is set to 1 indicating that the section of frame 510 that was encapsulated contained an EOF.

After packets 552, 554, 556, 558 are generated by gateway 135 and placed into ethernet packets, gateway 135 transmits the ethernet packets to gateway 175 by way of fabric 120. As described above in connection with the decapsulation process, gateway 175, depending on the contents of the DorK and EncapEOF bits replaces certain D28.5 words with K28.5 words. The EncapSeqCnt field is used to reconstruct, in the right order, the FC frame from the data segments that were placed in the four ethernet packets. The reconstructed FC frame is transmitted by gateway 175 to device 182 via FC enabled SAN 180. While the above described the gateway processing for an FC frame with a length greater than MTU, it should be appreciated that the gateway processing for an FC frame with a length smaller than MTU is substantially similar.

Figure 6:
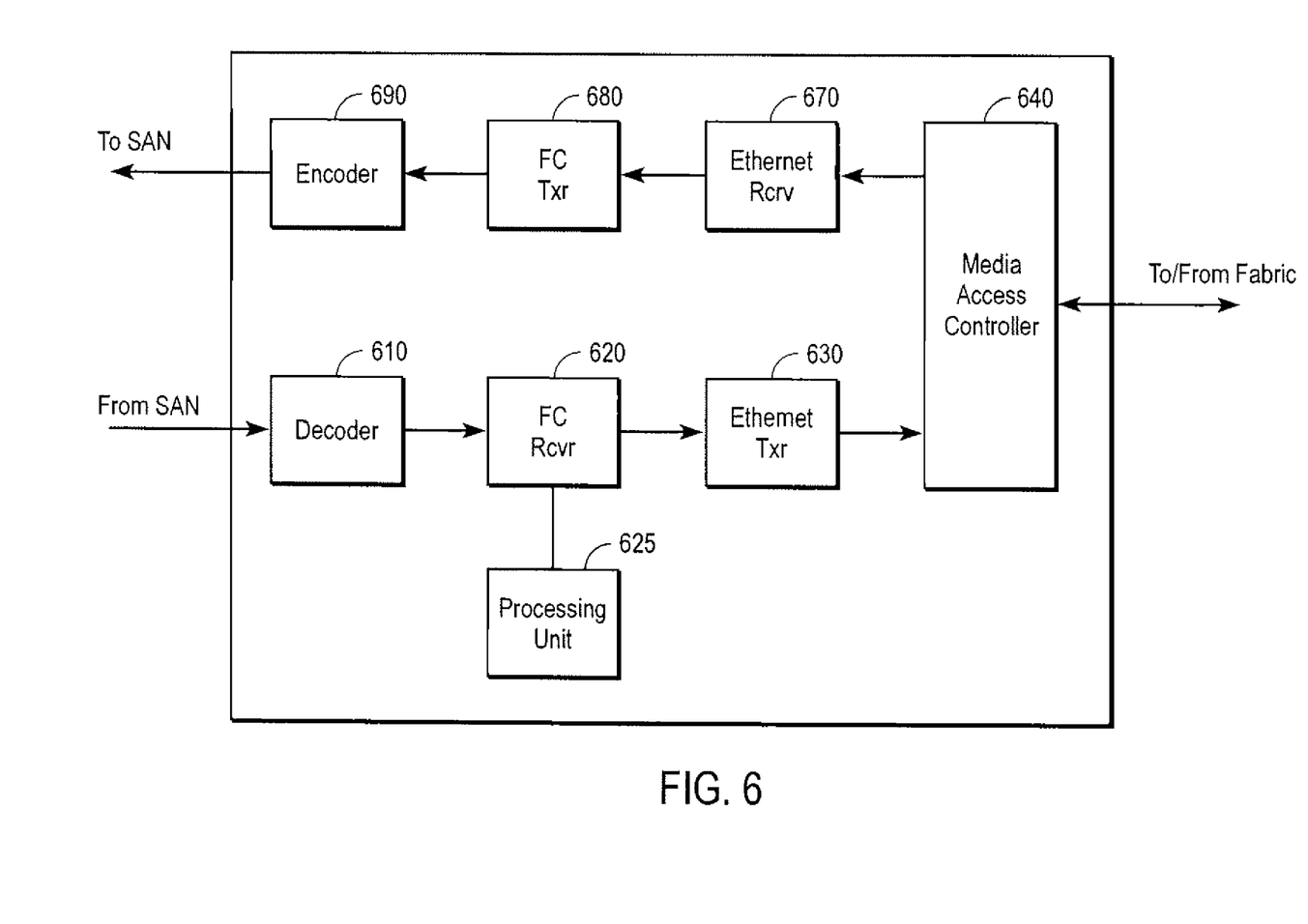
FIG. 6 illustrates a block diagram of a gateway's receive data path and transmit data path.

FIG. 6 illustrates a block diagram of a gateway's receive data path and transmit data path. Gateway receive data path 600 includes 10b/8b decoder 610, FC receiver 620, gigabit ethernet transmitter 630, and gigabit ethernet media access controller 640. Data path 600 is representative of the receive data path of gateways 135 and 175 (i.e., SAN-to-gateway-to-fabric data path). Decoder 610 receives from devices in a SAN (e.g., SAN 140) FC primitives, primitive sequences and data frames which are to be forwarded to another SAN (e.g., SAN 180) that is coupled to fabric 120. Decoder 610 converts every 10 bits that are received into a byte in accordance with the International Business Machines (IBM) 8b/10b decoding scheme. Decoder 610 then forwards each byte to receiver 620. Receiver 620 composes a sequence out of the bytes it receives and determines whether the sequence is to be forwarded to fabric 120. If the sequence is to be forwarded to fabric 120, receiver 620 sends it to transmitter 630. If the sequence is to be used by the gateway for flow analysis, it is forwarded to a processing unit 625. If the sequence has a length that exceeds one MTU, transmitter 630 divides the sequence into several segments each of which is as large as the MTU. Transmitter 630 then encapsulates the segments and replaces control characters, as required, in accordance with the encapsulation scheme described above. If the sequence has a length that is less than or equal to an MTU, transmitter 630 encapsulates the segment and replaces control characters, as required, in accordance with the encapsulation scheme described above. After encapsulation, each segment is forwarded to controller 640 which composes an ethernet packet for the segment. Controller 640 composes an ethernet packet(s) with the encapsulated segment(s) as the ethernet packet payload(s). Controller 640 transmits the ethernet packet(s) across fabric 120 which transports them to a gateway which is coupled to the SAN and which is supposed to be the recipient of the FC signals in the ethernet packet data payload(s).

Figure 7:
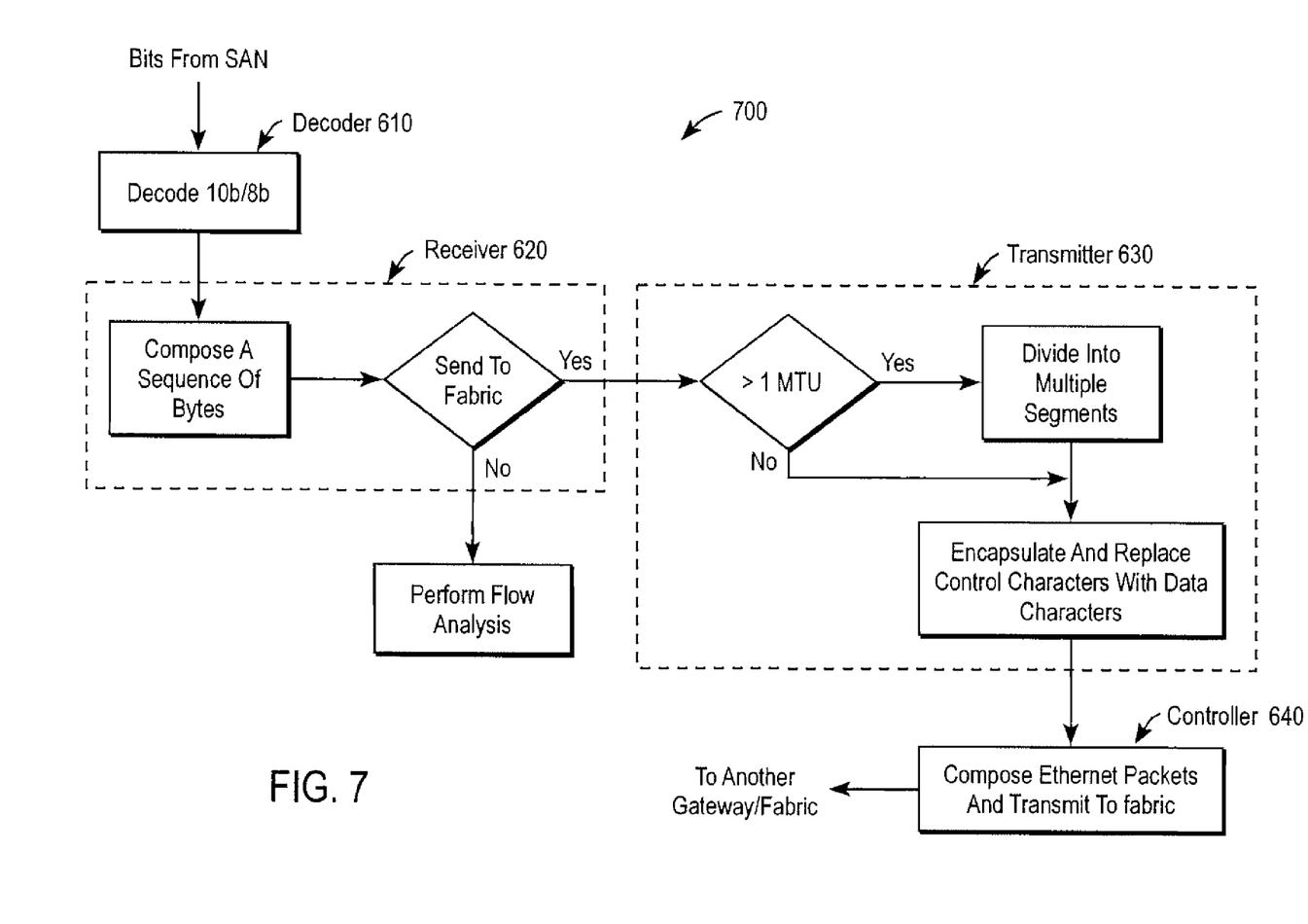
FIG. 7 illustrates a flow diagram of the operations performed by a gateway receive data path.

FIG. 7 illustrates a flow diagram of the operations performed by a gateway receive data path. Diagram 700 shows, according to one embodiment, the operations performed by each unit in the gateway receive data path. It should be appreciated that in an alternative embodiment operations may be performed by a unit other than the one indicated in diagram 700.

Gateway transmit data path 650 includes 8b/10b encoder 690, FC transmitter 680, gigabit ethernet receiver 670, and gigabit ethernet media access controller 640. Transmit data path 650 is representative of the transmit data path of gateways 135 and 175 (i.e., fabric-to-gateway-to-SAN data path). Media access controller 640 receives from a router (not shown) in fabric 120 bytes which are to be composed into ethernet packet(s). Media access controller 640 composes ethernet packet(s) out of the received bytes and forwards the ethernet packet(s) to ethernet receiver 670. The ethernet packet(s) has a data payload(s) containing encapsulated FC primitives, primitive sequences and data frames which are to be forwarded to a SAN coupled to the gateway. Ethernet receiver 670 determines whether the ethernet packet payload(s) are to be forwarded to a SAN. If the ethernet packet payloads are to be forwarded to a SAN, receiver 670 removes the ethernet packet payloads from the ethernet packets and sends the payloads to transmitter 680. If the packet payloads are not to be forwarded to a SAN, receiver 670 sends the ethernet packet to the appropriate device. Transmitter 680 decapsulates the bytes in the ethernet packet payload(s) and reconstructs an FC frame: if necessary, from more than one ethernet packet payload. Transmitter 680 forwards the decapsulated bytes and the reconstructed FC frames, if any, to Encoder 690. Encoder 690 converts every byte into 10 bits in accordance with the IBM 8B/10B encoding scheme and then transmits the converted bytes to device 182 via server 188.

If transmitter 680 reconstructs an abridged primitive sequence, transmitter 680 continuously generates the words of the primitive sequence and provides them to encoder 690. In this manner, device 182 receives a stream of words of the type found in the abridged primitive sequence. The type of words in the stream will change when transmitter 680 reconstructs, at a later time, an abridged primitive sequence of a different type.

Figure 8:
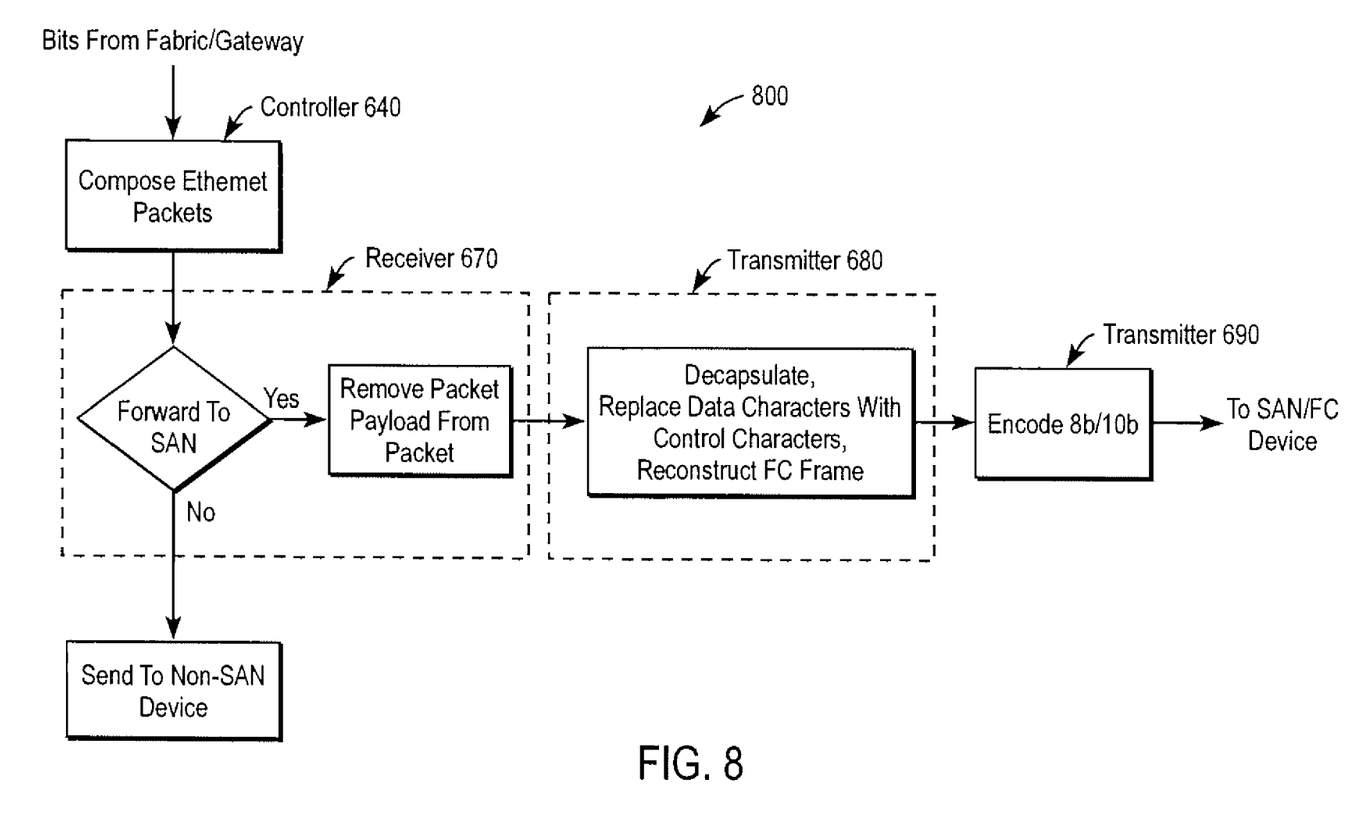
FIG. 8 illustrates a flow diagram of the operations performed by a gateway transmit data path.

FIG. 8 illustrates a flow diagram of the operations performed by a gateway transmit data path. Diagram 800 shows, according to one embodiment, the operations performed by each unit in the gateway transmit data path. It should be appreciated that in an alternative embodiment operations may be performed by a unit other than the one indicated in diagram 800.

While according to an embodiment network 140 and 180 operated in accordance with American National Standards Institute (ANSI) X3.-240-1994, Fibre Channel Physical and Signaling Interface specification, for the Fibre Channel protocol (also known as FC-PH), it should be appreciated that SANs 140 and 180 are not limited to operation in accordance with FC-PH. Rather, in alternative embodiments in accordance with the present invention, networks 140 and 180 can operate in accordance with other Fibre Channel specifications or modifications to FC-PH, including the following: ANSI X3.297-997, Fibre Channel Physical and Signaling Interface-2 (FC-PH-2), and Project 119-D, Fibre Channel Physical and Signaling Interface—3 (FC-PH-3). All the various Fibre Channel protocols will be collectively referred to as FC. While according to an embodiment fabric 120 operates in accordance with the Gigabit Ethernet protocol, it should be appreciated that in alternative embodiments in accordance with the present invention, fabric 120 operates in accordance with Asynchronous Transfer Mode (ATM), Synchronous Optical Network (SONET), and Internet Protocol (IP) and other communication protocols. While in one embodiment fabric 120 is a network of multiple routers and other devices, in an alternative embodiment fabric 120 can be as simple as a single router/bridge which operates in accordance with a protocol different from the protocol of SANs 140 and 180.

While according to one embodiment networks 140 and 180 have the topology shown in FIG. 1, it should be apparent that in alternative embodiments in accordance with the present inventions either or both of networks 140 and 180 can have a different topology from that shown in FIG. 1. Furthermore, the exact nature of the topologies, data rates, media types and connectors is not particularly crucial to the practice of the present invention. While in one embodiment SANs 140 and 180 are combinations of storage devices, it should be appreciated that in alternative embodiments SANS 140 and 180 can include other data sources such as tape drives, compact disk (CD) drives, computers, and digital imaging or sound equipment. Furthermore, in alternative embodiments SANs 140 and 180 can consist of only one data source.

While in one embodiment K28.5 characters are changed to D28.5 characters, it should be appreciated that in alternative embodiments K28.5 characters can be mapped to other characters. While in one embodiment operation is based on words, in an alternative embodiment other units for measuring information may be used.

Thus, a method and apparatus for communicating between two FC enabled devices that are coupled by a non-FC enabled fabric has been described. Although the present invention has been described with reference to specific exemplary embodiments, it will be evident to one of ordinary skill in the art that various modifications and changes may be made to these embodiments without departing from the broader spirit and scope of the invention as set forth in the claims. Accordingly, the specification and drawings are to be regarded in an illustrative rather than a restrictive sense.

We claim:

1. A method for communicating between a first Fibre Channel (FC) enabled device and a second FC enabled device, where the communication occurs across a fabric that operates in accordance with a first protocol different from a FC protocol of the first and second FC enabled devices, the method comprising:
   receiving, from the first FC enabled device, at a first gateway receiver a sequence of bytes including at least one FC control character in accordance with the FC protocol;
   replacing the at least one FC control character with at least one first protocol data character that represents the at least one FC character;
   generating at least one of an encapsulation header and an encapsulation footer; the step of generating including setting at least one of:
   an FC control character indicator in the encapsulation header if a first byte in the sequence of bytes received at the first gateway receiver contains the first protocol data character that represents the at least one FC character, and
   an FC end of frame indicator in the encapsulation footer if a last byte in the sequence of bytes received at the first gateway receiver contains the first protocol data character that represents the at least one FC character.

2. The method of claim 1, further comprising encapsulating the sequence of bytes with the at least one of the encapsulation header and encapsulation footer.

3. The method of claim 1, wherein the first protocol is gigabit ethernet.

4. The method of claim 1, wherein the at least one control character is a K28.5 character.

5. The method of claim 1, wherein the at least one data character is a D28.5 character.

6. The method of claim 2, further comprising:
   placing at a controller the encapsulated sequence of bytes in a packet composed in accordance with the first protocol to produce a packetized encapsulated sequence; and
   transmitting, through the fabric, from the controller to a second gateway receiver the packetized encapsulated sequence.

7. The method of claim 6, wherein the transmitting by the controller is performed at a transmission rate, and the receiving at the first gateway receiver is performed at a reception rate that is less than the transmission rate.

8. The method of claim 6, further comprising:
   receiving at the second gateway receiver the packetized encapsulated sequence;
   removing the encapsulation header and the encapsulation footer; and
   replacing the at least one first protocol data character with the at least one FC control character to produce a regenerated sequence of bytes.

9. The method of claim 8, wherein replacing the at least one first protocol data character results in an end of file FC control character being placed in the regenerated sequence of bytes.

10. The method of claim 8, further comprising transmitting the regenerated sequence of bytes to the second FC enabled device.

11. The method according to claim 6 wherein the packetized encapsulated sequence is transmitted a plurality of N times prior to a subsequent first protocol data transfer operation.

12. The method according to claim 6 wherein the packetized encapsulated sequence is received by the first intermediate network gateway receiver a plurality of N times prior to the receipt by the first intermediate network gateway receiver of a subsequent first protocol data transfer operation.

13. A gateway for communicating among a first device and a second device, both of which operate in accordance with a fibre channel (FC) protocol, and an intermediate network coupling the first device to the second device and having a first protocol, the gateway comprising:
   a first FC protocol gateway receiver that is to receive a sequence of bytes including at least one FC control character in accordance with the FC protocol;
   a first intermediate network gateway transmitter that is to replace the at least one FC control character with at least one intermediate network data character that represents the at least one FC control character and to generate an encapsulation header and an encapsulation footer; and
   wherein the transmitter is to set a FC control character indicator in the encapsulation header if a first byte in the sequence of bytes received at the FC protocol gateway receiver is a FC control character, and to set an end of frame indicator in the encapsulation footer if another byte in the sequence of bytes received at the first FC protocol gateway receiver is an end of frame FC control character.

14. The gateway of claim 13, wherein the transmitter encapsulates with the encapsulation header and the encapsulation footer the sequence of bytes in which at least one control character was replaced with at least one data character.

15. The gateway of claim 13, further comprising a controller that is to place the encapsulated sequence of bytes in a packet composed in accordance with the first protocol to produce a packetized encapsulated sequence and that is to transmit, through the intermediate network, from the controller to the second device the packetized encapsulated sequence.

16. The gateway of claim 13, wherein the first protocol is gigabit ethernet.

17. The gateway of claim 13, wherein the at least one control character is a K28.5 character.

18. The gateway of claim 13, wherein the at least one data character is a D28.5 character.

19. The gateway of claim 14, further comprising a controller that is to place the encapsulated sequence of bytes in a packet composed in accordance with the first protocol to produce a packetized encapsulated sequence and that is to transmit, through the intermediate network, from the controller to a second gateway receiver, the packetized encapsulated seqeunce.

20. The gateway of claim 19, wherein the controller is to transmit at a transmission rate, and the receiving at the first gateway receiver is performed at a reception rate that is less than the transmission rate.

21. The gateway according to claim 19 wherein the packetized encapsulated sequence is transmitted a plurality of N times prior to a subsequent first protocol data transfer operation.

22. A gateway for communicating among a first device and a second device, both of which operate in accordance with a fibre channel (FC) protocol, and an intermediate network coupling the first device to the second device and having a first protocol, the gateway comprising:

a first intermediate network gateway receiver that is to receive a packetized encapsulated sequence in accordance with the first protocol from the intermediate network and to determine whether the packetized encapsulated sequence contains bytes that include therein at least one intermediate network data character representation of an FC control character to be forwarded to the first device;

wherein the first intermediate network gateway receiver is to depacketize the packetized encapsulated sequence to produce an encapsulated sequence and to forward the encapsulated sequence to the first device if the packetized encapsulated sequence contains bytes that include therein the representation of the FC control character; and a first FC network gateway transmitter that is to receive the encapsulated sequence, to remove an encapsulation header and an encapsulation footer from the encapsulated sequence to produce a decapsulated sequence, and to replace in the decapsulated sequence the at least one intermediate network data character representing the FC control character with the at least one FC control character if an indicator in at least one of the header or footer indicates replacement.

23. The gateway of claim 22, further comprising an encoder that is to transmit to the first device in accordance with the FC protocol the decapsulated sequence.

24. The gateway of claim 23, wherein a controller is to receive at a receive rate, and the encoder transmits at a transmission rate less than the receive rate.

25. The gateway of claim 22, wherein the first protocol is gigabit ethernet.

26. The gateway of claim 22, wherein the at least one control character is a K28.5 character.

27. The gateway of claim 22, wherein the at least one data character is a D28.5 character.

* * * * *

UNITED STATES PATENT AND TRADEMARK OFFICE
CERTIFICATE OF CORRECTION

| | | |
|---|---|---|
| PATENT NO. | : 7,114,009 B2 | Page 1 of 1 |
| APPLICATION NO. | : 09/811155 | |
| DATED | : September 26, 2006 | |
| INVENTOR(S) | : Loren M. Jones et al. | |

It is certified that error appears in the above-identified patent and that said Letters Patent is hereby corrected as shown below:

On title page, item 75 Inventors
Replace "Stanford L. Helton, San Jose, CA" with --Sanford L. Helton, San Jose, CA--.

Signed and Sealed this

Seventeenth Day of July, 2007

JON W. DUDAS
*Director of the United States Patent and Trademark Office*